(12) United States Patent
Husebø et al.

(10) Patent No.: US 9,841,368 B2
(45) Date of Patent: Dec. 12, 2017

(54) SENSOR SYSTEM FOR CORROSION MONITORING

(71) Applicant: TeCom AS, Bergen (NO)

(72) Inventors: Magne Husebø, Bergen (NO); Jon Oddvar Hellevang, Bergen (NO); Peter James Thomas, Bergen (NO)

(73) Assignee: TECOM AS, Bergen (NO)

( * ) Notice: Subject to any disclaimer, the term of this patent is extended or adjusted under 35 U.S.C. 154(b) by 109 days.

(21) Appl. No.: 14/654,838

(22) PCT Filed: Dec. 19, 2013

(86) PCT No.: PCT/NO2013/050230
§ 371 (c)(1),
(2) Date: Jun. 22, 2015

(87) PCT Pub. No.: WO2014/098613
PCT Pub. Date: Jun. 26, 2014

(65) Prior Publication Data
US 2015/0346159 A1     Dec. 3, 2015

(30) Foreign Application Priority Data
Dec. 20, 2012   (NO) .................................. 20121544

(51) Int. Cl.
*G01N 29/07* (2006.01)
*G01N 17/04* (2006.01)
*G01N 29/24* (2006.01)

(52) U.S. Cl.
CPC ........... *G01N 17/046* (2013.01); *G01N 17/04* (2013.01); *G01N 29/07* (2013.01);
(Continued)

(58) Field of Classification Search
None
See application file for complete search history.

(56) References Cited

U.S. PATENT DOCUMENTS 5,337,376 A * 8/1994 Ravetti .............. G01N 21/7703
                                                250/227.14
6,004,639 A * 12/1999 Quigley ................ B29C 70/086
                                                138/125
(Continued)

FOREIGN PATENT DOCUMENTS

WO    WO 2009/002180    12/2008

OTHER PUBLICATIONS

Mousumi Majumder et al., *Fibre Bragg Gratings in Structural Health Monitoring—Present Status and Applications*, Sensors and Actuators A., Elsevier Sequoia S.A., Lausanne, CH, vol. 147, No. 1, Sep. 15, 2008, pp. 150-164.

(Continued)

*Primary Examiner* — Paul West
*Assistant Examiner* — Mark A Shabman
(74) *Attorney, Agent, or Firm* — Hershkovitz & Associates, PLLC; Abe Hershkovitz

(57) ABSTRACT

A permanently installed monitoring system for corrosion under insulation (PIMSCUI) and a method for performing the monitoring of said system are provided. The objective of the invention by a fiber optic cable permanently mounted between walls of a pipeline and pipeline insulation surrounding the pipeline and placement of acoustic emitters along the length of the pipeline in mechanical contact with the optical fiber. The acoustic emitters send a pulsed acoustic signal towards the pipeline which is received by the optical fiber, the acoustic signal subsequently travels through the pipeline wall, reflecting from the inner diameter of the pipeline before the reflected pulse is received at the optical fiber.

17 Claims, 1 Drawing Sheet

(52) U.S. Cl.
CPC ..... *G01N 29/2418* (2013.01); *G01N 29/2475* (2013.01); *G01N 2291/0258* (2013.01); *G01N 2291/02845* (2013.01); *G01N 2291/02854* (2013.01); *G01N 2291/0421* (2013.01); *G01N 2291/0422* (2013.01); *G01N 2291/0423* (2013.01); *G01N 2291/0427* (2013.01)

(56) References Cited

U.S. PATENT DOCUMENTS

| | | | |
|---|---|---|---|
| 6,100,969 | A | 8/2000 | Perez |
| 2008/0260324 | A1* | 10/2008 | Takahashi .............. G01B 17/02 385/12 |
| 2010/0141281 | A1 | 6/2010 | Johnsen |
| 2012/0019105 | A1 | 1/2012 | Krohn et al. |
| 2012/0092960 | A1 | 4/2012 | Gaston et al. |
| 2012/0294124 | A1 | 11/2012 | Krohn et al. |

OTHER PUBLICATIONS

Hideo Cho et al., *Monitoring of Corrosion Under Insulations by Acoustic Emission and Humidity Measurement*, Journal of Nondestructive Evaluation, Kluwer Academic Publishers-Plenum Publishers, NE, vol. 30, No. 2, Feb. 4, 2011, pp. 59-63.

International Search Report dated May 9, 2014 in PCT Application No. PCT/NO2013/050230.

Norwegian Search Report dated Jul. 23, 2013 in the related Norwegian Application No. 20121544.

* cited by examiner

SENSOR SYSTEM FOR CORROSION MONITORING

BACKGROUND OF THE INVENTION

Technical Field

The invention relates to corrosion monitoring in general, and more specifically, to a permanently installed system for monitoring corrosion under insulation (PIMSCUI), and a method for performing the monitoring system.

Background Art

Pipeline and process vessel corrosion under insulation is an enormous and costly problem across northern European oil and gas installations, and similar weather-related challenges are likely to face other growing markets around the world such as those in Canada and Brazil. At present, corrosion under insulation (CUI) detection is a slow manual process requiring skilled inspectors with costly inspection tools. There are no permanent monitoring systems available suitable for CUI purposes. Enormous direct cost reductions could be achieved through better decision making enabled by permanent monitoring technology. Savings would be magnified through the reduction of indirect costs such as CUI-related shutdowns.

One prior art method is referred to in published US Patent Application No. US 2010/0141281 A1 based on PCT Publication No. WO 2009/002180 by Johnsen, disclosing fiber optic based humidity measurements. The problem is that such a measurement system lacks a mechanism to confirm that corrosion has taken place. Furthermore, the system of WO/2009/002180 refers to the implementation of a grid or line of discrete and spaced humidity sensors, and as such, the humidity can only be measured where the discrete sensing elements exist.

Also of interest is the method in published US Patent Application No. US 2012/294124 A1, regarding monitoring of corrosion in a pipe.

Published US Patent Application No. US 2012/092960 A1 discloses a system having distributed acoustic sensors, wherein an optical fiber is used for distribution of signals.

SUMMARY OF THE INVENTION

Therefore, a main objective of the present invention is to provide a permanently installed monitoring system for corrosion under insulation (PIMSCUI), and a method for performing the monitoring of such a system.

In one embodiment, permanently installed fiber optic technology for monitoring corrosion under insulation (CUI) continuously over large surface areas is provided. The technology revolves around monitoring discrete or continuous moisture under insulation using fiber optics, alone or in combination with direct measurements for CUI. The direct measurements can either be spot measurements or quantities averaged over any given length of the installation. The technology has extremely low installation overhead demands: minimal power cabling is required, and signal transmission is through the fiber optic sensing cable.

The objective is achieved according to the invention by a sensor system for corrosion monitoring as defined in the appended claims.

The present invention attains the above-described objective by a fiber optic cable permanently mounted between walls of a pipeline and pipeline insulation surrounding the pipeline, and placement of acoustic emitters along the length of the pipeline in mechanical contact with the optical fiber. The acoustic emitters send a pulsed acoustic signal towards the pipeline which is received by the optical fiber, and the acoustic signal subsequently travels through significant depths of the pipeline wall, if desired, up to the extent that the wave is reflecting from the inner diameter of the pipeline before the reflected pulse is received at the optical fiber.

A technical difference of the present invention over that disclosed in WO 2009/002180 is the use of acoustic emitters. The effect of this is the ability to use acoustic means to probe corrosion conditions while the fiber is used to act as an acoustic signal receptor. A second technical difference is that the humidity sensing elements need not necessarily be discrete, and could give spatially continuous measurement profiles over significant lengths.

Furthermore, the chemical sensing capability of the invention described herein extends to one or more of a family of corrosion-related parameters comprising humidity, liquid water, pH, conductivity, salinity and hydrogen.

These effects provide in turn several further advantageous effects:

it makes it possible to confirm that corrosion has taken place irrespective of the current or previous level of humidity;

it makes it possible to confirm the likelihood that corrosion has taken place irrespective of the current or previous level of humidity;

it makes it possible to probe the humidity at all points along the fiber, with a resolution limited only by the instrumentation; and it makes it possible to probe a range of other corrosion-related chemical parameters at all points along the fiber, with a resolution limited only by the instrumentation.

BRIEF DESCRIPTION OF THE DRAWINGS

The above and further features of the invention are set forth with particularity in the appended claims and, together with advantages thereof, will become clearer from consideration of the following detailed description of an embodiment of the invention given with reference to the accompanying drawings.

The invention will be further described below in connection with exemplary embodiments which are schematically shown in the drawings, wherein.

DESCRIPTION OF THE REFERENCE SIGNS

The following reference numbers and signs refer to the drawings:

| | |
|---|---|
| 100 | Measurement system |
| 200 | Pipeline/Vessel wall |
| 210 | Pipeline/Vessel inner wall |
| 220 | Pipeline/Vessel outer wall |
| 250 | Pipeline/Vessel insulation |
| 260 | Pipeline/Vessel insulation inner wall |
| 270 | Pipeline/Vessel insulation outer wall |
| 300 | Optical fibre |
| 310 | Optical fibre core |
| 320 | Optical fibre cladding |
| 330 | Humidity sensitive material, or material sensitive to one or more of liquid water, pH, conductivity, salinity and hydrogen |
| 340 | Protective jacket |
| 400 | Acoustic emitter |
| 410 | Piezo element |
| 420 | Controller |
| 430 | Power source |
| 440 | Clamp |
| 450 | Excited beam |
| 460 | Reflected beam |
| 500 | Remote signal receiver |

DETAILED DESCRIPTION

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

Figure 1:
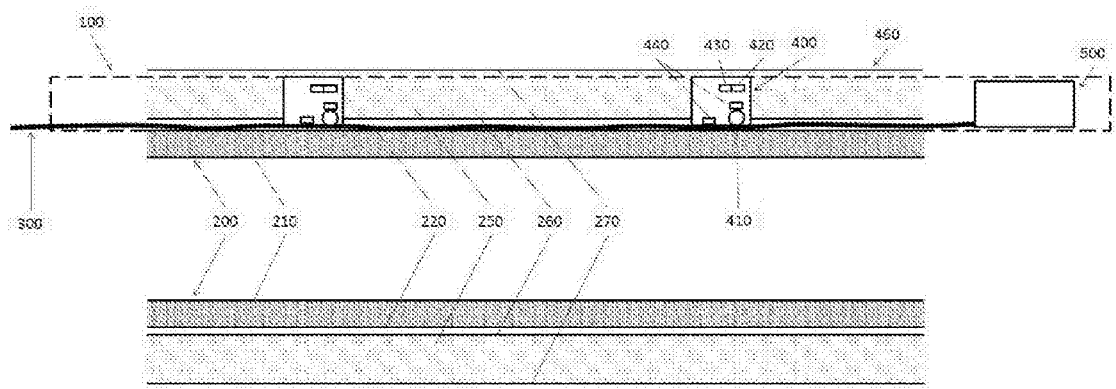
FIG. 1 shows an embodiment for distributed monitoring of corrosion under insulation.

The invention will be further described in connection with exemplary embodiments which are schematically shown in the drawings, wherein FIG. 1 shows a typical embodiment of a measurement system 100 installed on a pipeline 200 having an inner wall 210 and an outer wall 220. The pipeline is further provided with a pipeline insulation 250 having an outer wall 270 and an inner wall 260 preferably in close contact with the pipeline outer wall 220.

Figure 3:
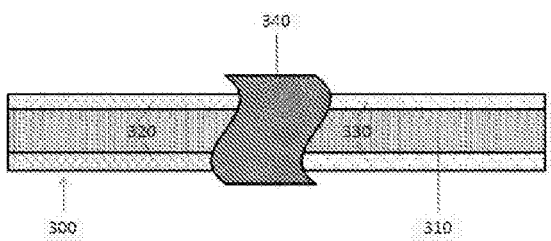
FIG. 3 shows an embodiment for fiber used for spatially continuous measurement of one or more of a group of corrosion related chemical parameters comprising humidity measurement, liquid water, pH, conductivity, salinity and hydrogen. The cladding is partially removed or partially tapered, and replaced with a humidity sensitive material, or a material sensitive to one of the chemical parameters in the previously mentioned group.

An optical fiber 300 is positioned between the outer wall 220 of a pipeline and the inner wall 260 of the pipeline insulation 250 surrounding the pipeline 200. A fiber comprises typically a core 310 surrounded by a cladding 320, see FIG. 3.

At least one acoustic emitter 400 is positioned along the length of the pipeline in mechanical contact with the optical fiber. Each acoustic emitter comprises means for emitting an acoustic signal, typically a piezo element 410, means for providing operating power, typically a battery 430, and a clamp 440 for providing mechanical attachment.

Figure 2:
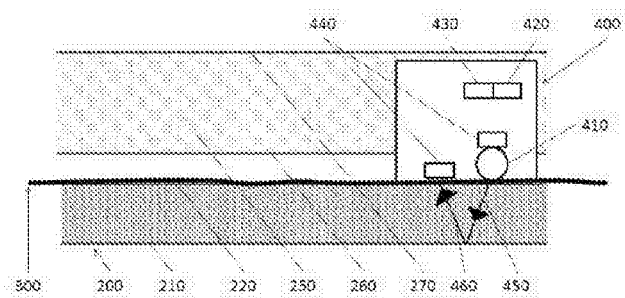
FIG. 2 shows an embodiment for pipeline/vessel wall-thickness measurement.

Each acoustic emitter sends an excited beam 450 of a pulsed signal towards the pipeline 200 (see FIG. 2) which is received by the optical fiber 300, and the acoustic signal subsequently travels through significant depths of the pipeline wall 270, if desired up to the extent that the wave is reflecting from the inner wall 260 of the pipeline before the reflected pulse is received at the optical fiber as the reflected beam 460. The inward travelling and back reflected acoustic signals are converted to the optical properties of the light travelling through the fiber at the points the signals are received. These signals are then transmitted to a remote location. The time difference between the detection of the inward and outward travelling pulses is used to calculate the path of the acoustic pulse through the pipeline wall, which is a function of the pipeline wall thickness. The thickness of pipeline walls is a well-known quantity for the determination of the extent of pipeline corrosion, and forms the basis of various inspection and monitoring technologies [Clampon 2012, GE 2012]. The position and form of the acoustic emitters and optical sensing elements could be adjusted in order to excite and detect arbitrary acoustic modes, including Lamb waves, controlling the sensitivity and coverage area of the mode.

The excited signal is emitted from the acoustic unit, typically by a piezo element. The excited and reflected signals are detected by the fiber, typically a suitable optical method for converting the acoustic signals to fiber transmitted optical signals includes the use of fiber Bragg gratings. Other methods for encoding the acoustic signal include, but are not limited to, the use of Distributed Acoustic Sensing (DAS, see Optasense 2012) or elements introducing microbend losses into the fiber, detectable using, e.g., optical time domain reflectometry (OTDR) methods.

Pipeline wall thickness measurements could be made at various points along the pipeline with the use of multiple acoustic emitters and optical multiplexing techniques. The acoustic emitters could be user controlled through wireless communication, or operate as independent units activating at predetermined time intervals.

Figure 4:
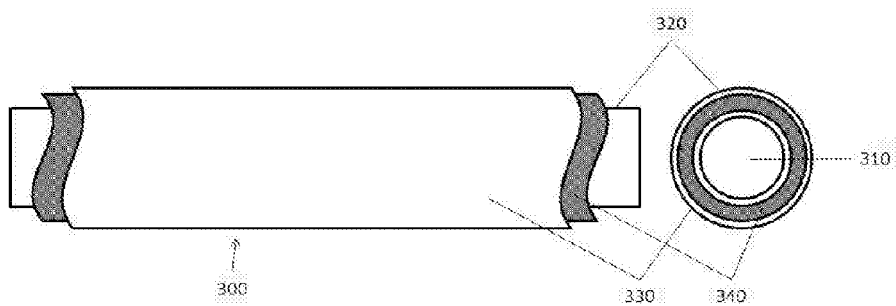
FIG. 4 shows an embodiment for fiber used for spatially continuous humidity measurement. The cabled optical fiber is surrounded with a humidity sensitive material.

The clamps 440 should be located such that the inward travelling acoustic wave is effectively transmitted through the optical fiber and into the pipeline/vessel wall. The clamps should also ensure effective transmission of the reflected outwardly travelling acoustic wave into the optical fiber from the pipeline/vessel wall, A second property of the system is that the fiber used for transmitting the acoustic signals has optomechanical properties that are a function of the humidity in the surrounding space between the pipeline and insulation. Humidity is a known precursor to the development of corrosion. Materials such as di ureasil (Correia, 2012) and PVA/COCl2 (Cho, 2011) compounds could be used to surround the fiber to give it the desired optomechanical optical properties. Using such materials, the ambient humidity could be converted to a loss parameter of the fiber, probed for example using optical time domain reflectometry (OTDR) methods. In such an embodiment, the humidity sensitive material 330 would typically replace part or all of the fiber cladding 320 which would be partially removed or tapered, see FIG. 3. Exposed fiber coating or humidity sensitive material could be partially or completely covered with a protective jacket 340 to increase mechanical strength. The protective jacket may or may not be permeable to water. The loss would typically result from a refractive index or absorption change of the humidity sensitive material. Alternatively, the loss information could be transferred to cladded (and possibly also cabled) fiber by coating the cladding or cable with a humidity sensitive material, see FIG. 4. In such an embodiment, the sensitive material would typically have mechanical properties that change with humidity and would be arranged in such a way to induce losses into the fiber as a function of humidity, see FIG. 4. Alternatively, humidity could be converted to a strain in the optical fiber, measurable using for example using non-linear optical scattering methods (distributed strain sensing, DSS, see Sensornet 2012). Typically for this type of embodiment, the humidity sensitive material would have mechanical properties that change with humidity, and be located on the outside of the cladding (and possibly suitable cable also) in order to prevent loss. The use of OTDR and DSS methodologies would allow for significant lengths of optical cable to act as a single humidity sensor, with each unit length being independently probed for humidity within the limiting spatial resolution given by the light sources, transmission medium and detectors. The described modes for humidity detection also apply to the measurement of one or more of the setup of parameters indicating corrosion; presence of liquid water, pH, conductivity, salinity and hydrogen, where the humidity sensitive material is replaced with suitable material for these purposes.

A number of variations on the above-described method can be envisaged. For instance, a person skilled in the art will see that the acoustic emitters can be operated in two modes.

In a first mode, the wall thickness is measured at a single point. In this mode, the acoustic emitter and receiver, typically the sensitive fiber element, are positioned at substantially the same point along the pipeline, with the acoustic wave propagating substantially perpendicular to the pipeline. The wall thickness is derived from the propagation time of the acoustic wave for the forward and return pass through the pipeline wall.

In a second mode, an average pipeline wall thickness is measured. In this mode, an acoustic emitter positioned at a specific point along the pipeline wall sends a guided Lamb wave through the pipeline wall to a receiver positioned further along the pipeline.

The propagation time of the Lamb wave is a function of the average wall thickness between the emitter and receiver. The present invention also makes it possible to employ modes in the group containing longitudinal waves, transverse waves, shear waves, Rayleigh waves, Stonely Waves, Sezawa waves and Love waves, in order to assess the physical condition of the pipeline. This invention makes it also possible to measure a second acoustic reflection indicating solid build-up at a pipe inner wall (e.g., sand, scale, asphaltenes, waxes), cracking, pitting, density variations and other material degradation and deficiencies. The fiber can also be used for communications such as for additional instruments communicating through the fiber 10 infrastructure, including instruments for measuring salinity and temperature. The fiber can be used as part of a distributed sensing system, specifically those that measure temperature, strain, and acoustic signals. The fiber can also be used for measuring additional parameters that could act as corrosion indicators, such as the presence of liquid water, humidity, salinity, pH, conductivity and hydrogen. Additional parameters could also be measured for the purpose of compensating for environmental effects on other corrosion indicator measurements.

In another embodiment, the invention monitors the wear and degradation of components internal to the pipeline/process vessel. This can be achieved by measuring the evolution in space and time of (i) acoustic signals transmitted through the pipeline wall, (ii) temperature, and (iii) the previously-named parameters that act as corrosion indicators.

In a further embodiment, a reference fiber is used, running parallel with the sensing fiber. The reference fiber could be used, for example, to compensate for the influence of temperature on the sensing fiber. The reference fiber could also be used to compensate for other environmental or system-related effects on the sensing fiber.

In another embodiment, the humidity and acoustic sensing elements are on separate optical fibers.

In yet another embodiment, the excited and reflected acoustic signals are detected by a technology other than fiber optics, the detected signal is then encoded on the optical fiber by some means such as an amplified acoustic signal or electro optical protocols.

In a further embodiment, the optical fibers are single lengths, or comprised of discrete sections that are assembled into one continuous length before, during or after the installation process. A modularized embodiment would be particularly compatible with modern insulation systems that comprise many discrete insulating units.

In a further embodiment, the acoustic emitter and receiver are replaced with other instrumentation that measures pipe vessel wall material degradation such as pitting, cracking and the presence of hydrogen. In such cases, the fiber could be used as a medium to transmit data from these instruments to a remote location.

INDUSTRIAL APPLICABILITY

The invention according to the application finds use in continuous monitoring, typically for offshore applications and other places where access is hard or limited, such as in nuclear reactors.

REFERENCES

Clampon 2012, Clampon website; http://www.clampon.com/?page=2&show=7
GE 2012, GE website; http://www.ge-mcs.com/en/ultrasound/corrosion-monitoring/rightrax-automate-lt.html
Correia, S, F. H. et. al. 2012 "Optical Fiber Relative Humidity Sensor Based on a FBG with a Di-Ureasil Coating" Sensor, 12, 8847-8860.
Cho, H., et. al. 2011, "Monitoring of Corrosion Under Insulations by Acoustic Emission and Humidity measurement" J. Nondestruct. Eval. 30, 59-63
Johnsen 2010, US patent US20100141281
Sensornet 2012, Sensornet website, accessible at http://www.sensornet.co.uk/technology/distributed-strain-sensing/index.html
Optasense 2012, Optasense website, accessible at http://www.optasense.com/

The invention claimed is:

1. A sensor system for monitoring corrosion in a pipeline/vessel wall, said sensor system comprising:
an optical fiber provided with a receiver for converting an acoustic signal to an optical signal,
at least one acoustic emitter positioned at a specific point along the wall sending an acoustic wave from the group comprising consisting of 'lamb waves', longitudinal waves, transverse waves, shear waves, Rayleigh waves, Stonely waves, Sezawa waves and Love waves through the wall to a receiver positioned further along the wall,
wherein the propagation time of said acoustic wave is a function of the average wall thickness, between the emitter and the receiver, wherein during the operations, the acoustic emitter emits an excited beam which then is reflected as a reflected beam which then is received by the optical fiber, wherein the fiber is further provided with a sensitive material that allows for corrosion related chemical parameters to be measured in a continuous fashion over the length of the fiber.

2. A sensor system for monitoring corrosion in a pipeline/vessel wall, comprising:

an optical fiber configured to receive and convert an acoustic signal into an optical signal;

at least one acoustic emitter positioned at a specific point along the wall to emit at least one acoustic wave from the group consisting of longitudinal waves, transverse waves, shear waves, Rayleigh waves, Lamb waves, Stonely waves Sezawa waves and Love waves through the wall to a receiver positioned at a different point along the wall from the specific point where the emitter is positioned;

wherein a propagation time of said wave is a function of the average wall thickness between the emitter and receiver;

wherein the acoustic emitter emits an excited beam which then is reflected as a reflected beam which then is received by the optical fiber; and wherein the fiber is further provided with a sensitive material that allows for corrosion related chemical parameters to be measured in a continuous fashion over the length of the fiber.

3. The sensor system according to claim 2, wherein the chemical parameter is one of liquid water, humidity, salinity, pH and conductivity.

4. The sensor system according to claim 2, wherein the acoustic signal is converted to an optical signal based on the use of Bragg gratings.

5. The sensor system according to claim 2, wherein the acoustic emitter and the fiber are positioned at substantially the same point along the wall, with the acoustic wave propagating substantially perpendicular to the wall, wherein the wall thickness is derived from the propagation time of the acoustic wave for the propagation through the pipeline wall.

6. A method for operating a sensor system for monitoring corrosion in a pipeline/vessel wall according to claim 2, comprising:

emitting an excited beam from an acoustic emitter,
receiving a reflected beam from a surface of the wall,
determining an amount of corrosion based on at least one of thickness, level of cracking, pitting and density variations, measured from the emitted beam and the reflected beam.

7. The method according to claim 6, wherein further acoustic reflections are measured, indicating solid build-up at pipe inner wall.

8. The sensor system according to claim 2, wherein the sensor monitors wear and degradation of components internal to the pipeline/process vessel.

9. The sensor system according to claim 8, wherein the monitoring is achieved by measuring the evolution in space and time of (i) acoustic signals transmitted through the pipeline wall, (ii) temperature, and (iii) the chemical parameters that act as corrosion indicators.

10. The sensor system according to claim 2, wherein a reference fiber runs parallel with the sensing fiber.

11. The sensor system according to claim 10, wherein the reference fiber compensates for the influence of temperature on the sensing fiber.

12. The sensor system according to claim 11, wherein the reference fiber also compensates for other environmental or system-related effects on the sensing fiber.

13. The sensor system according to claim 2, wherein the humidity and acoustic sensing elements are on separate optical fibers.

14. The sensor system according to claim 2, wherein the excited and reflected acoustic signals are detected by a technology other than fiber optics, the detected signal is then encoded on the optical fiber by one of, an amplified acoustic signal or electro optical protocols.

15. The sensor system according to claim 2, wherein the optical fibers are one of, (a) single lengths, or (b) discrete sections that are assembled into one continuous length before, during or after the installation process.

16. The sensor system according to claim 2, wherein the acoustic emitter and receiver are replaced with other instrumentation that measures pipe vessel wall material degradation of at least one of, pitting, cracking and the presence of hydrogen.

17. A sensor system for monitoring corrosion in a pipeline/vessel wall, comprising:

an optical fiber configured to receive and convert an acoustic signal into an optical signal;

at least one acoustic emitter positioned at a specific point along the wall to emit at least one acoustic wave from the group consisting of longitudinal waves, transverse waves, shear waves, Rayleigh waves, Lamb waves, Stonely waves Sezawa waves and Love waves through the wall to a receiver positioned at a different point along the wall from the specific point where the emitter is positioned;

wherein a propagation time of said wave is a function of the average wall thickness between the emitter and receiver;

wherein, during operations, the acoustic emitter emits an excited beam which then is reflected as a reflected beam which then is received by the optical fiber;

wherein the fiber is further provided with a sensitive material that allows for corrosion related chemical parameters to be measured in a continuous fashion over the length of the fiber;

wherein the chemical parameter is one of liquid water, humidity, salinity, pH and conductivity;

wherein the acoustic signal is converted to an optical signal based on the use of Bragg gratings;

wherein the acoustic emitter and the fiber are positioned at substantially the same point along the wall, with the acoustic wave propagating substantially perpendicular to the wall; and wherein the wall thickness is derived from the propagation time of the acoustic wave for the propagation through the pipeline wall.

* * * * *